(12) United States Patent
Chamberlain

(10) Patent No.: US 6,470,730 B1
(45) Date of Patent: Oct. 29, 2002

(54) DRY TRANSFER METHOD FOR THE PREPARATION OF EXPLOSIVES TEST SAMPLES

(75) Inventor: Robert T. Chamberlain, Mays Landing, NJ (US)

(73) Assignee: The United States of America as represented by the Secretary of Transportation, Washington, DC (US)

( * ) Notice: Subject to any disclaimer, the term of this patent is extended or adjusted under 35 U.S.C. 154(b) by 315 days.

(21) Appl. No.: 09/640,660

(22) Filed: Aug. 18, 2000

(51) Int. Cl.[7] .............................................. G01N 17/00
(52) U.S. Cl. ...................................................... 73/1.03
(58) Field of Search ................................ 73/1.01, 1.02, 73/1.03, 1.06, 863.21, 863.71; 250/252.1; 436/8, 9, 19, 901

(56) References Cited

U.S. PATENT DOCUMENTS 5,134,875 A * 8/1992 Jensen et al. ................. 73/1.03
5,502,998 A * 4/1996 Miller et al. .................. 73/1.06
5,604,295 A * 2/1997 Robinson ..................... 73/1.06
5,741,984 A * 4/1998 Danylewych-May et al. ............... 73/864.71

* cited by examiner

Primary Examiner—Robert Raevis
(74) Attorney, Agent, or Firm—Otto M. Wildensteiner

(57) ABSTRACT

A method of preparing samples for testing explosive and drug detectors of the type that search for particles in air. A liquid containing the substance of interest is placed on a flexible Teflon® surface and allowed to dry, then the Teflon® surface is rubbed onto an item that is to be tested for the presence of the substance of interest. The particles of the substance of interest are transferred to the item but are readily picked up by an air stream or other sampling device and carried into the detector.

15 Claims, No Drawings

DRY TRANSFER METHOD FOR THE PREPARATION OF EXPLOSIVES TEST SAMPLES

STATEMENT OF GOVERNMENT INTEREST

The present invention may be made or used by or for the Government of the United States without the payment of any royalties thereon or therefor.

BACKGROUND

One of the fastest methods of screening a large number of people or items for the presence of explosives or drugs on them is to draw a sample of air across each person or item and then see if the air contains explosive particles or drug residue. This is a quick, non-intrusive, and effective method of determining if the person or item has been in contact with explosives or drugs.

A problem arises, however, in testing and calibrating the device which is used to measure the presence of the substance of interest. The problem is in duplicating the way that the substances get placed on and released from the surfaces of items touched by terrorists such as luggage handles, packages, etc. and their clothing. In addition, the amount of explosive or drug on a person or item differs if the person or item has had substantial contact (i.e. the person has manufactured an explosive device or been directly involved in a drug transaction) or only casual contact with the substance (i.e. money that was in a bank drawer and came in contact with other money that had been used in a drug transaction or handled by someone who had been working with explosives). This latter requires the development of test samples having different (known) levels of explosives or other substances on them.

The prior art method was to make a liquid suspension of the explosive or other substance of interest, then apply this suspension to an item. After the suspension had dried, the item was then passed through the detection portal where an air sample was taken and analyzed for the presence of explosive particles or drug residue. The problem was that if the explosive or drug had been deposited on a rough or textured surface it would settle in the grooves of the surface, and very little would be drawn into the sampled air. Thus the detector would fail to report the presence of explosives or drugs in an unacceptably high number of cases. If the suspension were applied to cloth, the particles would be carried between the fibers of the cloth by capillary action and would not be picked up by the air stream, again resulting in a false negative report.

OBJECTS OF THE PRESENT INVENTION

Accordingly, it is an object of the present invention to provide a method of preparing test samples that simulate the properties of real items that contain minute-quantities of explosives or drugs on their surfaces.

It is a further object of the present invention to provide such a method wherein the quantity of explosive or drug can be varied.

It is a further object of the present invention to provide such a method which is quick and easy and which produces reliable results.

SUMMARY

Briefly, the present invention comprises the steps of preparing a liquid containing the explosive or other substance of interest, placing some of the liquid on a Teflon® coated surface, allowing the liquid to dry, and then rubbing the coated Teflon® on an item, thereby transferring the explosive or other substance of interest to the surface of the item.

DESCRIPTION OF THE PREFERRED EMBODIMENT

Tests have shown that drugs or explosives that were transferred from a person's hands or fingers to a rough or textured solid surface or a piece of cloth are readily released from that surface and will be picked up by an air stream. The prior art method of directly depositing a liquid suspension of drugs or explosives on a surface caused the granules to settle in the grooves in the solid surface or to be drawn between the fibers of the cloth by capillary action. With either type surface, the granules would not be readily picked up by an air stream or by wiping with a cloth or other sampling device and therefore would not be detected, resulting in a false negative.

In the method of the present invention, the explosive or other substance of interest is usually suspended in water or other volatile carrier that does not dissolve the substance of interest. In most cases the water or other carrier should not dissolve the substance of interest because it is desired to deposit the usual size granules or grains on the items that will be tested for the presence of the substance of interest. If the substance were dissolved, it would possibly result in a very fine powder after the carrier evaporated, and this would not give realistic results. However, it has been found that plastic explosives such as C4, Detasheet, and Semtex give better results when they are dissolved in a suitable carrier. For example, C4 dissolved in acetone works well.

The liquid is deposited on the surface of a flexible Teflon® strip and allowed to dry. After it dries, the substance of interest (i.e. explosive, drugs, etc.) is in the form of a layer of normal size granules that can be transferred very easily to another surface by rubbing. This prevents the problem with the prior art method of directly depositing the suspension on the surface; the problem with this method is that the granules settle in the grooves in a rough or textured solid surface, and get drawn between the fibers of cloth by capillary action. With either type of surface, solid or cloth, the granules cannot be easily picked up by the air stream or sampling device, and this results in a false negative reading for the substance of interest. By contrast, when a properly prepared Teflon® strip is rubbed on a rough or textured solid surface the granules of the substance of interest are transferred to the surface but do not settle in the grooves in the surface as they do when applied in a liquid suspension. Likewise, when the Teflon® strip is rubbed on cloth the granules are transferred to the surface of the cloth, not drawn between the fibers as when directly deposited while still in suspension.

The Teflon® strip is prepared by removing the vinyl support sheet from a strip of Bytac® Type VF-81 0.001 inch thick Teflon® bonded to 0.002 inch vinyl support sheet, manufactured by Norton Performance Plastics Corporation of Akron, Ohio. The Bytac® sheet is then stuck to a piece of ordinary manila file folder material by means of the adhesive which was used to stick it to the vinyl support sheet. This is then cut into 1 inch by 3 inch strips to be used in preparing the test samples.

To prepare the samples, a suspension was prepared by placing the substance of interest in water. This suspension was stirred thoroughly and then was placed on one of the Bytac® strips and allowed to dry, usually overnight. The concentration of substance of interest varied between 4 and 15 micrograms per milliliter of water. This variation resulted from the fact that the ultimate objective was to place a certain quantity of the substance of interest on the cloth or solid item rather than deposit a certain concentration of suspension on the Bytac® strip and transfer this amount to the item to be tested. The amount of substance of interest was determined by making a bomb, for instance, and then grasping a briefcase handle and then testing the briefcase handle to see how much explosive residue was transferred to the handle. Tests were then run to determine how much of the substance had to be on the Bytac® in order to transfer the desired amount to the briefcase handle. If the concentration of substance in water was too low, several applications would be made to the Bytac® strip and allowed to dry in order to put the proper quantity on the strip.

The substance of interest was then transferred to a solid object or a piece of cloth to determine how well it could be detected. The solid object was a solid vinyl briefcase handle, since it was felt that this is an object that would be touched by someone who had been working with drugs or explosives. Tests have shown that optimum transfer of particles to a solid surface is achieved by rubbing the surface with the coated Bytac® strip 8 times back and forth over the same location, with moderate pressure. This transfers the maximum amount of the substance of interest, which can then be picked up by an air stream and carried into the detector.

When transferring the substance of interest to a piece of cloth, the Bytac® strips are prepared the same way. The prepared strips are then wiped across the cloth 2 times in the same direction, again with moderate pressure. The test cloth was usually muslin, since muslin is a very porous material and any test that works with muslin will work with almost any other cloth. The substance of interest on the Bytac® strip would transfer to the outer surface of the cloth rather than soaking into the fibers as with the prior art method, and could be easily and repeatedly removed by an air stream or other sampling device and taken into a detector. This is the method by which cloth is usually contaminated by drugs or explosives, since they are normally powders that get deposited on clothing, etc. rather than liquid suspensions that soak into cloth.

Tests run on samples prepared in this way show accurate, reproducible results that can be used to calibrate and or test detectors used in airports, etc. While the above description has been directed to preparing samples of drugs and explosives, it obviously can be used to prepare samples of almost any other substance of interest. Likewise, while the carrier liquid described above is water, any other appropriate volatile liquid can be used. Likewise, the carrier liquid should not leave behind a film which may interfere with the transfer of the substance of interest to an item, or a residue which may interfere with the detection of the substance of interest after it has been transferred to an item.

Although the term Teflon® has been used to describe the flexible surface on which the liquid suspension is deposited, any other material can be used so long as it is flexible and allows the dried substance of interest to be transferred to another surface as described above. The preferred flexible surface is Bytac™, a form of Teflon® made by Performance Plastics Corp. of Akron, Ohio, because of its superior flexibility.

I claim:

1. The method of preparing samples for testing to determine the presence of a substance of interest which comprises preparing a liquid containing the substance of interest; depositing said liquid on a flexible Teflon® surface; allowing said liquid to dry; transferring said substance of interest on said Teflon(& surface to an item; and testing said item to determine the presence of said substance of interest.

2. The method of claim 1 wherein said liquid is prepared by suspending or dissolving said substance of interest in a liquid.

3. The method of claim 1 wherein said step of transferring said substance of interest on said flexible Teflon® surface to an item comprises rubbing said flexible Teflon® surface on said item.

4. The method of claim 3 wherein said step of rubbing said flexible Teflon® surface on said item comprises rubbing said Teflon® surface in both directions eight times in the same location on said item with moderate pressure when said item comprises a solid surface.

5. The method of claim 3 wherein said step of rubbing said flexible Teflon® surface on said item comprises rubbing said Teflon® surface twice in the same direction with moderate pressure when said item comprises a cloth surface.

6. The method of claim 2 wherein said liquid is water.

7. The method of claim 2 wherein said liquid is acetone.

8. The method of claim 2 wherein said substance of interest is an explosive.

9. The method of claim 2 wherein said substance of interest is a narcotic.

10. The method of claim 2 including making a sufficient number of deposits of said liquid on said Teflon® surface to place a predetermined amount of said substance of interest onto said Teflon® surface.

11. The method of preparing samples for testing to determine the presence of a substance of interest which comprises preparing a liquid containing said substance of interest; depositing said liquid on a non-porous flexible surface; allowing said liquid to dry; transferring said substance of interest on said non-porous flexible surface to an item; and testing said item to determine the presence of said substance of interest.

12. The method of claim 11 wherein said liquid is prepared by placing said substance of interest in a liquid which does not leave behind a film which can interfere with the transfer of said substance of interest to an item.

13. The method of claim 11 wherein said liquid is prepared by placing said substance of interest in a liquid which does not leave behind a residue which can interfere with the detection of said substance of interest on an item.

14. The method of claim 11 including making a sufficient number of deposits of said suspension on said non-porous flexible surface to place a predetermined amount of said substance of interest onto said flexible non-porous surface.

15. The method of claim 11 wherein said step of transferring said substance of interest on said non-porous flexible surface comprises rubbing said non-porous flexible surface on said item.

* * * * *